US 8,717,029 B2

(12) United States Patent
Chae et al.

(10) Patent No.: US 8,717,029 B2
(45) Date of Patent: May 6, 2014

(54) APPARATUS FOR MEASURING PERMITTIVITY OF ROCKS AND FAULT CLAYS USING PERMITTIVITY SENSOR

(75) Inventors: Byung-Gon Chae, Daejeon (KR); Jung-Hae Choi, Daejeon (KR); Yong-Je Kim, Daejeon (KR)

(73) Assignee: Korea Institute of Geoscience and Mineral Resources (KIGAM), Daejeon (KR)

( * ) Notice: Subject to any disclaimer, the term of this patent is extended or adjusted under 35 U.S.C. 154(b) by 226 days.

(21) Appl. No.: 13/294,642

(22) Filed: Nov. 11, 2011

(65) Prior Publication Data

US 2012/0293180 A1 Nov. 22, 2012

(30) Foreign Application Priority Data

May 18, 2011 (KR) .................. 10-2011-0046775

(51) Int. Cl.
*G01V 3/00* (2006.01)
*E21B 43/00* (2006.01)
(52) U.S. Cl.
CPC .. *G01V 3/00* (2013.01); *E21B 43/00* (2013.01)
USPC ........... 324/347; 324/353; 324/323; 324/341; 324/376; 324/377; 175/40; 175/48; 175/50; 73/152.05; 73/152.07; 73/152.08; 73/152.09; 73/866; 73/152.11
(58) Field of Classification Search
CPC .................................. G01V 3/00; E21B 43/00
USPC ......... 324/347, 353, 323, 341, 376–377, 698; 324/693, 629, 633, 636, 637, 638, 639; 175/40, 48, 50; 73/152.05, 152.07, 73/152.08, 152.09, 866, 152.11
See application file for complete search history.

(56) References Cited

U.S. PATENT DOCUMENTS

| | | | | | |
|---|---|---|---|---|---|
| 2,811,038 | A | * | 10/1957 | Karol | 73/823 |
| 3,420,093 | A | * | 1/1969 | Collins | 73/38 |
| 3,611,799 | A | * | 10/1971 | Davis | 73/152.24 |
| 4,626,773 | A | * | 12/1986 | Kroeger et al. | 324/642 |
| 4,703,277 | A | * | 10/1987 | Kenyon et al. | 324/323 |
| 4,912,415 | A | * | 3/1990 | Sorensen | 324/347 |
| 5,058,425 | A | * | 10/1991 | Davis et al. | 73/152.11 |
| 5,083,088 | A | * | 1/1992 | Bereskin | 324/632 |
| 5,187,443 | A | * | 2/1993 | Bereskin | 324/632 |
| 5,275,063 | A | * | 1/1994 | Steiger et al. | 73/865.6 |

(Continued)

OTHER PUBLICATIONS

Adisoemarta et al., "Electrical Impedance Variation With Frequency in Shales and Shaly Sands", 67th Annual Technical Conference and Exhibition of the SPE, 1992, p. 131-142.*

(Continued)

*Primary Examiner* — Patrick J Assouad
*Assistant Examiner* — Lamarr Brown
(74) *Attorney, Agent, or Firm* — Ladas & Parry LLP (57) ABSTRACT

An apparatus for measuring permittivity of a sample. The apparatus includes: a sample chamber including a sealed space portion in which a sample to be measured is put; a pressure adjusting unit for varying pressure by applying water pressure to the space portion of the sample chamber; a permittivity sensor for measuring permittivity of the sample and disposed outside the sample chamber; measurement conducting wires including conductors, installed to contact the sample and connected to the permittivity sensor by using electric wires; and a data logger for storing data relating to permittivity that is measured by the permittivity sensor.

11 Claims, 6 Drawing Sheets

(56) References Cited

U.S. PATENT DOCUMENTS

| | | | |
|---|---|---|---|
| 5,328,849 A * | 7/1994 | Smith | 436/32 |
| 5,811,973 A * | 9/1998 | Meyer, Jr. | 324/338 |
| 6,453,727 B1 * | 9/2002 | Lenormand et al. | 73/38 |
| 6,910,535 B2 * | 6/2005 | Tare et al. | 166/250.14 |
| 7,124,819 B2 * | 10/2006 | Ciglenec et al. | 166/264 |
| 7,128,142 B2 * | 10/2006 | Heathman et al. | 166/53 |
| 7,363,160 B2 * | 4/2008 | Seleznev et al. | 702/7 |
| 7,546,885 B2 * | 6/2009 | Longfield | 175/50 |
| 8,443,661 B1 * | 5/2013 | Bi | 73/152.11 |
| 2005/0028974 A1 * | 2/2005 | Moody | 166/264 |
| 2005/0104596 A1 * | 5/2005 | Fleury | 324/376 |
| 2005/0152432 A1 * | 7/2005 | Hakimuddin | 374/53 |
| 2006/0117841 A1 * | 6/2006 | Mango | 73/152.11 |
| 2006/0186897 A1 * | 8/2006 | Niemann | 324/633 |
| 2008/0087470 A1 * | 4/2008 | Villareal et al. | 175/50 |
| 2008/0236891 A1 * | 10/2008 | Huynh et al. | 175/48 |
| 2009/0126475 A1 * | 5/2009 | Zhang et al. | 73/152.05 |
| 2009/0126996 A1 * | 5/2009 | Villareal et al. | 175/50 |
| 2009/0306898 A1 * | 12/2009 | Anschutz et al. | 702/11 |
| 2010/0153958 A1 * | 6/2010 | Richards et al. | 718/104 |
| 2010/0324868 A1 * | 12/2010 | Russell et al. | 703/1 |
| 2011/0210757 A1 * | 9/2011 | Bismarck et al. | 324/693 |
| 2011/0271751 A1 * | 11/2011 | Brooks et al. | 73/152.07 |
| 2012/0160018 A1 * | 6/2012 | Jones et al. | 73/61.71 |
| 2013/0002258 A1 * | 1/2013 | Ligneul et al. | 324/376 |
| 2013/0020074 A1 * | 1/2013 | Kischkat et al. | 166/250.01 |
| 2013/0151154 A1 * | 6/2013 | Nutley et al. | 702/6 |

OTHER PUBLICATIONS

Chen et al., "Archie Parameter Determination by Analysis of Saturation Data", Petrophysics, vol. 43, Mar.-Apr. 2002), p. 103-107.*
Timur, "Advances in Well Logging", Society of Petroleum Engineers of AIME, Jun. 1982, p. 1181-1185.*
Sharma et al., "Release and Deposition of Clays in Sandstones", Society of Petroleum Engineers of AIME, 1985, p. 125-139.*
Patil et al., "Experimental Study of Electrical Properties of Oil-Based Mud in the Frequency Range From 1 to 100 MHz", Sep. 2010 SPE Drilling & Completion, p. 380-390.*

* cited by examiner

APPARATUS FOR MEASURING PERMITTIVITY OF ROCKS AND FAULT CLAYS USING PERMITTIVITY SENSOR

CROSS-REFERENCE TO RELATED PATENT APPLICATION

This application claims the benefit of Korean Patent Application No. 10-2011-0046775, filed on May 18, 2011, in the Korean Intellectual Property Office, the disclosure of which is incorporated herein in its entirety by reference.

BACKGROUND OF THE INVENTION

1. Field of the Invention

The present invention relates to an apparatus for measuring permittivity of material, and more particularly, to an apparatus for measuring permittivity of material that is put in a high pressure environment, such as rocks, a fault material or the like.

2. Description of the Related Art

High level radioactive wastes should be safely isolated from the human environment and an ecosystem for at least several hundred thousand years to several million years. To this end, geological disposal is performed. In other words, in geological disposal, a place for disposing radioactive wastes is constituted in parent rocks formed at a depth of 500 to 1,000 mm from the underground, and the radioactive wastes are disposed at the place. More specifically, cavities are formed in salt layers with low porosity and a high compressive strength, clay layers with a good absorption property or hard rocks so that high level radioactive wastes are stored in the cavities.

After the Kyoto protocol has been published, significance of carbon dioxide ($CO_2$) management is gradually increasing. Salt layers in deep underground or reservoir layers on which cap rocks are formed, are used in establishing CCS facilities for storing $CO_2$.

In addition, in compressed air energy storage systems that have been briskly studied, methods of storing compressed air in deep underground have been suggested.

In order to store and keep gas, wastes or the like in deep underground, sufficient research and data relating to deep underground are required. For example, when radioactive wastes are stored in cavities that are formed in parent rocks in deep underground, exact data relating to a moisture content and porosity of rocks in high pressure deep underground is required to design the cavities so as to prevent leakage of radioactive wastes. In addition, such experiments should be carried out on various temperature conditions as well as various pressure conditions, and data relating to the experiments should be obtained.

However, in the related art, there are no apparatuses for measuring physical properties of parent rocks, for example, permittivity, by making a similar environment to deep underground. Although there are moisture sensors or permittivity sensors for measuring a moisture content or porosity of a soil sample by measuring permittivity of soil, there are no apparatuses for measuring physical properties of rocks in deep underground. Thus, there are many limitations in designing a space of deep underground.

SUMMARY OF THE INVENTION

The present invention provides an apparatus for measuring permittivity of a sample having an improved structure in which permittivity of the sample may be measured by varying pressure and temperature conditions.

According to an aspect of the present invention, an apparatus for measuring permittivity of a sample, includes: a sample chamber including a sealed space portion in which a sample to be measured is put; a pressure adjusting unit for varying pressure by applying water pressure to the space portion of the sample chamber; a permittivity sensor for measuring permittivity of the sample and disposed outside the sample chamber; measurement conducting wires including conductors, installed to contact the sample and connected to the permittivity sensor by using electric wires; and a data logger for storing data relating to permittivity that is measured by the permittivity sensor.

The sample chamber may include a container and a cover for opening or closing the container, and the cover may include a body part in which a plurality of perforation holes and a connection port for applying the water pressure to the space portion are formed and which is inserted in the container and is combined with the container, and a combination ring that is inserted between an outer circumferential surface of the body part and an inner circumferential surface of the container, is screw-coupled to the container and secures the body part at the container.

A stepped stopping portion may be formed on an inner circumferential surface of the container, and the body part may be inserted in the container and may be supported on the stopping portion, and a plurality of through holes may be formed in the combination ring along a circumferential direction of the combination ring, and a ring-shaped groove portion may be formed in an outer circumferential surface of the body part along a circumferential direction of the body part, and a plurality of pins may be inserted in the plurality of through holes and may be engaged in the groove portion of the body part so that the body part and the combination ring are rotated relative to each other.

The pressure adjusting unit may include a pump for pumping high-pressure water into the sample chamber, a connection line for connecting the pump and the connection port to each other, an adjusting valve that is disposed in the connection line and opens or closes the connection line, and a pressure gauge that is installed at the connection line and measures pressure.

The apparatus may further include a temperature adjusting unit for varying temperature of the sample chamber. The temperature adjusting unit may include: an external chamber that surrounds the sample chamber, forms a space between the external chamber and the sample chamber and includes an inlet through which a fluid is injected in the space and an outlet through which the fluid is discharged from the space; water tanks in which the fluid is stored and which are connected to the inlet and the outlet of the external chamber, respectively, so that the fluid is circulated; and a temperature adjusting unit that is disposed between the water tanks and the external chamber and adjusts temperature of the fluid.

The temperature adjusting unit may include: an external chamber that surrounds the sample chamber, forms a space between the external chamber and the sample chamber and includes an inlet through which a fluid is injected in the space and an outlet through which the fluid is discharged from the space; and a partition that is ring-shaped and divides a space of the external chamber into an internal space and an external space, wherein the internal space and the external space of the external chamber communicate with each other via an upper portion of the partition, and wherein the inlet is connected to the internal space of the partition in a space formed between the external chamber and the sample chamber, and the outlet is connected to the external space of the partition in the space formed between the external chamber and the sample chamber.

A groove portion may be formed in a middle of the sample, and the measurement conducting wires may be installed to closely contact the sample along an inner circumferential surface of the groove portion, and after the measurement conducting wires and the electric wires are installed, the measurement conducting wires of the groove portion may be sealed by using a filling material that is filled in the groove portion.

A plurality of measurement conducting wires may be spiral-shaped or ring-shaped, and a plurality of perforation holes may be formed in an upper portion of the sample chamber, and the electric wires connected to the measurement conducting wires may be taken out from the sample chamber and may be exposed to the outside via different perforation holes.

According to an aspect of the present invention, an apparatus for measuring permittivity of a sample, includes: a plurality of sample chambers each comprising a sealed space portion in which a sample to be measured is put; a pressure adjusting unit for varying pressure by applying water pressure to the space portion of each of the plurality of sample chambers; a permittivity sensor for measuring permittivity of the sample and disposed outside each of the sample chambers; measurement conducting wires comprising conductors and installed to contact the sample and connected to the permittivity sensor by using electric wires; and a data logger for storing data relating to permittivity that is measured by the permittivity sensor.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Hereinafter, an apparatus for measuring permittivity of a sample, according to exemplary embodiments of the present invention will be described with reference to the accompanying drawings, in which the exemplary embodiments of the present invention are shown.

Figure 1:
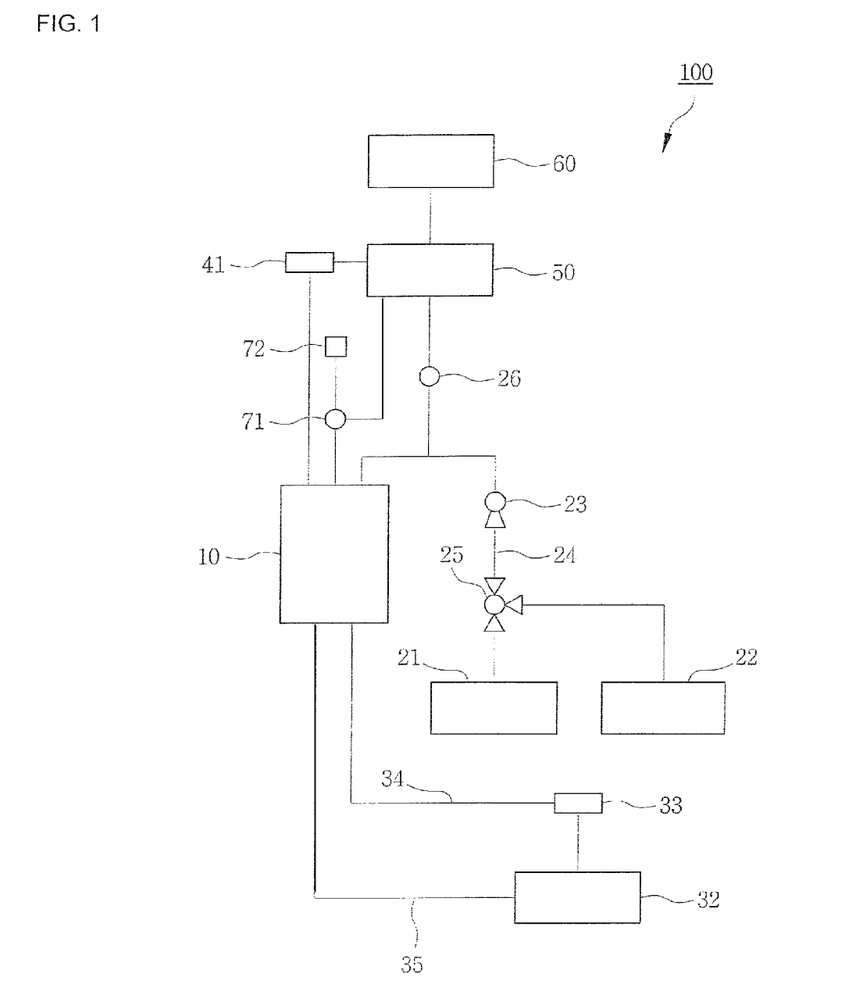
FIG. 1 is a schematic view of an apparatus for measuring permittivity of a sample, according to an embodiment of the present invention.
Figure 2:
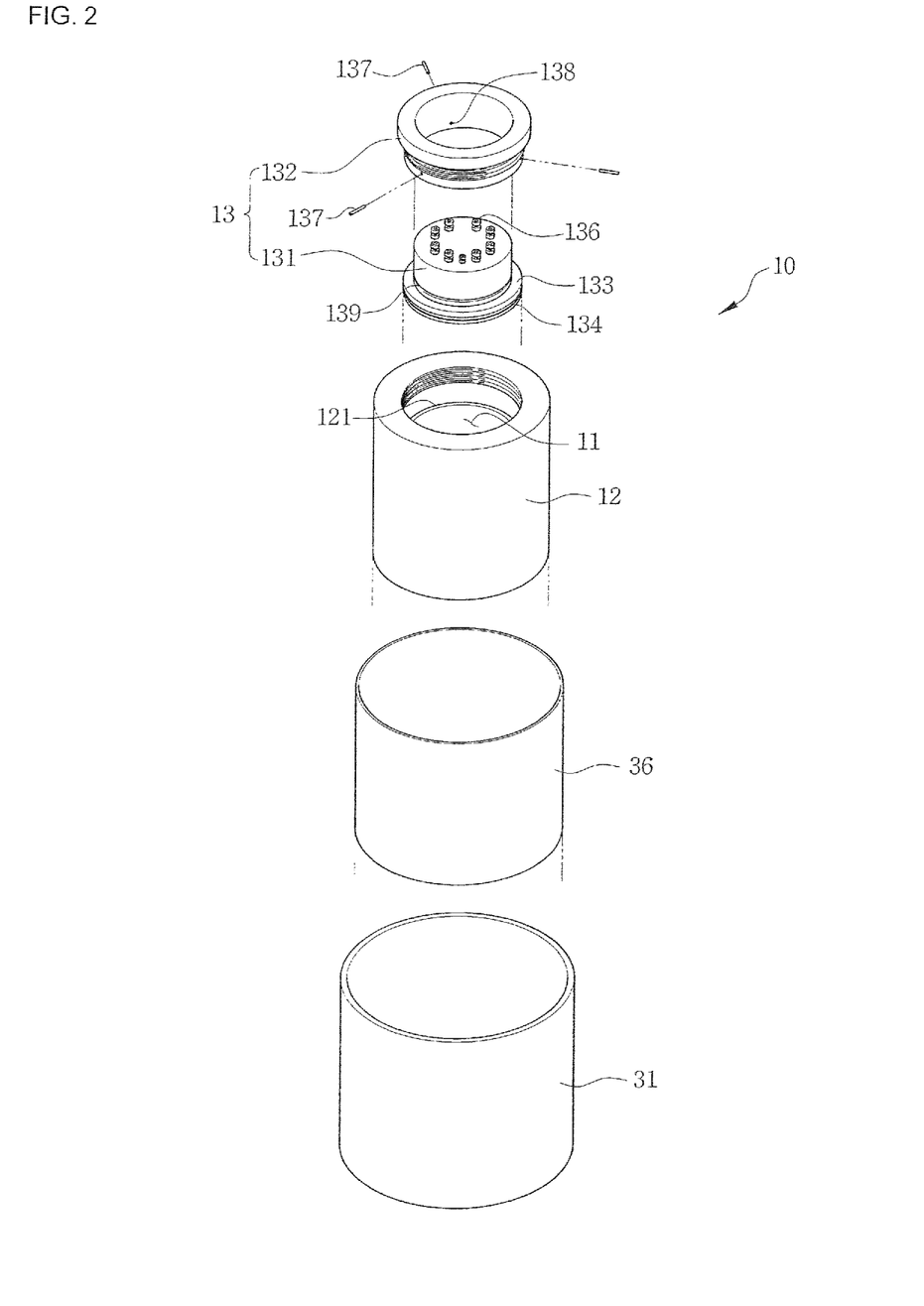
FIG. 2 is a schematic exploded perspective view of a sample chamber of the apparatus illustrated in FIG. 1.
Figure 3:
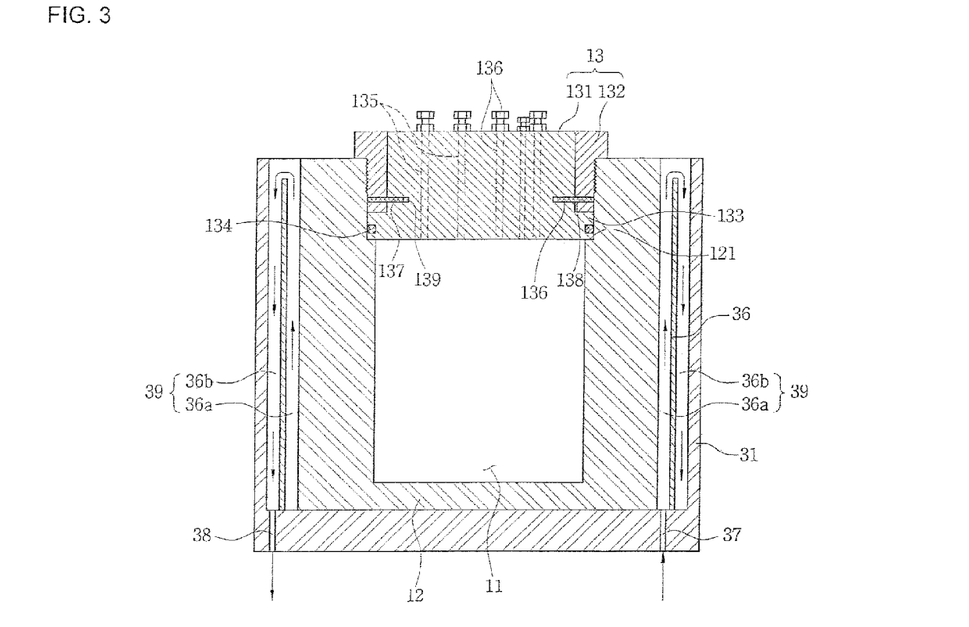
FIG. 3 is a schematic cross-sectional view illustrating the sample chamber combined with the apparatus of FIG. 1.

FIG. 1 is a schematic view of an apparatus 100 for measuring permittivity of a sample, according to an embodiment of the present invention, and FIG. 2 is a schematic exploded perspective view of a sample chamber 10 of the apparatus 100 illustrated in FIG. 1, and FIG. 3 is a schematic cross-sectional view illustrating the sample chamber 10 combined with the apparatus 100 of FIG. 1.

Referring to FIGS. 1 through 3, the apparatus 100 for measuring permittivity of a sample includes the sample chamber 10 and a pressure adjusting unit.

The sample chamber 10 provides a space portion 11 on which a sample (see S of FIG. 4) of which permittivity is to be measured, is put. The sample chamber 10 includes a container 12 and a cover 13. The cover 13 opens or closes the container 12. When the cover 13 closes the container 13, a closed space portion 11 is formed in the container 12.

In the current embodiment, the container 12 has an approximately cylindrical shape, and a bottom surface of the container 12 is closed, and a top surface thereof is opened. A stopping portion 121 is formed to have a stepped shape on an upper portion of an inner circumferential surface of the container 12.

In the current embodiment, the cover 13 includes a body part 131 and a combination ring 132. A flange portion 133 having a large diameter is formed on a lower portion of the body part 131 in such a way that the flange portion 133 is supported on the stopping portion 121 of the container 12. A groove portion is formed in the flange portion 133 along a circumferential direction of the flange portion 133, and an O-ring 134 is disposed on the groove portion. When the body part 131 is inserted in the container 12, the O-ring 134 is compressed between an outer circumferential surface of the flange portion 133 and an inner circumferential surface of the container 12 and seals the space portion 11 of the sample chamber 10.

Since an upper portion of the body part 131 has a small diameter, when the body part 131 is inserted in the container 12, a distance between the body part 131 and the inner circumferential surface of the container 12 is formed. The combination ring 132 is screw-coupled to a ring-shaped space. In other words, the combination ring 132 is ring-shaped, and a screw thread is formed at an outer circumferential surface of the combination ring 132, and a screw thread is formed at an upper portion of the inner circumferential surface of the container 12, resulting in the combination ring 132 screw-coupled to the container 12. When the combination ring 132 and the container 12 is screw-coupled to each other in this way, the combination ring 132 pressurizes the body part 131 downwards so that the body part 131 is secured at the container 12 and the space portion 11 is also fully sealed.

As described above, the reason why the cover 13 is divided into the body part 131 and the combination ring 132 is that relative rotation between the body part 131 and the combination ring 132 can be performed. In other words, a plurality of perforation holes 135 are formed in the body part 131 to pass through a space formed between top and bottom surfaces of the body part 131, and electric wires are inserted in the perforation holes 135 that will be described below. Thus, when the body part 131 is rotated so as to be combined with the container 12, electric wires may be twisted. Thus, in the current embodiment, relative rotation between the body part 131 and the combination ring 132 is possible, and the body part 131 is forcibly inserted in the container 12, and the combination ring 132 is screw-coupled to the container 12.

However, when the combination ring 132 and the body part 131 are separated from each other for relative rotation therebetween, it is inconvenient to do work. Thus, in the current embodiment, the body part 131 and the combination ring 132 are combined with each other by using a plurality of pins 137. In other words, a plurality of through holes 138 are formed in the combination ring 132 along a circumferential direction of the combination ring 132 to pass through a space formed between outer and inner circumferential surfaces of the combination ring 132, and a ring-shaped groove portion 139 in which the plurality of through holes 138 are to be engaged, is formed along an outer circumferential surface of the body part 131.

Thus, when the plurality of pins 137 are engaged in the groove portion 139 of the body part 131 after passing through the through holes 138, the combination ring 132 may be rotated relative to the body part 131 and is combined with the body part 131. Thus, when the combination ring 132 is screw-coupled to the container 12 or is unscrewed from the container 12, the body part 131 is also inserted in the container 12 or is separated from the container 12.

The pressure adjusting unit adjusts pressure in the sample chamber 10, and a variety of pressure adjusting units may be used. In the current embodiment, pressure in the sample chamber 10 is adjusted using water pressure.

The pressure adjusting unit includes two water tanks 21 and 22, a pump 23, and a connection line 24. The water tanks 21 and 22 include an injection water tank 21 in which water flowed in the sample chamber 10 is stored, and a discharge water tank 22 in which water discharged from the sample chamber 10 is stored. The connection line 24 connects the injection water tank 21 and the sample chamber 10 to each other. In other words, a connection port 136 is formed at the body part 131 of the sample chamber 10, and the connection line 24 is connected to the connection port 136, and water in the injection water bank 21 is transferred to an inside of the sample chamber 10. The connection line 24 is used as a discharge line for discharging water in the sample chamber 10 to the discharge water bank 22. In other words, a 3-way valve 25 is installed at the connection line 24 and may connect the connection line 24 to the injection water bank 21 or the discharge water bank 22 selectively.

The pump 23 is installed at the connection line 24 and pressurizes water in the injection water tank 21 against the sample chamber 10 by using a predetermined pressure. In addition, water in the sample chamber 10 may be discharged to the discharge water bank 22 in a reverse manner by using a bidirectional pump.

Pressure of the space portion 11 may be adjusted by applying water pressure to the space portion 11 of the sample chamber 10 by using the pump 23. A pressure gauge 26 is installed at the connection line 24, thereby measuring pressure in the sample chamber 10.

The apparatus 100 for measuring permittivity of a sample illustrated in FIG. 1 includes a temperature adjusting unit for varying temperature of the space portion 11 of the sample chamber 10.

The temperature adjusting unit includes an external chamber 31, a water tank 32, and a temperature adjusting device 33. The external chamber 31 is installed to surround the sample chamber 10, and a sealed fluid injection space 39 is formed between an inner circumferential surface of the external chamber 31 and the sample chamber 10.

The water tank 32 is connected to the fluid injection space 39 via a first connection tube 34 and a second connection tube 35. The first connection tube 34 is connected to an inlet 37 of the external chamber 31, and the second connection tube 35 is connected to an outlet 38 of the external chamber 31. Water in the water bank 32 is circulated in such a way that water in the water bank 32 is flowed in the fluid injection space 39 via the first connection tube 34 and is flowed back to the water tank 32 via the second connection tube 35. Although not shown, a pump is installed at a circulation path of water so as to circulate water.

The temperature adjusting device 33, in the current embodiment, a heater 33 is installed at the first connection tube 34, thereby adjusting temperature of water flowed in the fluid injection space 39. A thermometer 71 is attached to the sample chamber 10, measures temperature in the space portion 11 in real-time and is connected to a temperature display panel 72. Measured temperature may be displayed on the temperature display panel 72 so that a user may check the temperature in real-time.

In the current embodiment, the fluid injection space 39 is divided into an internal space 36a and an external space 36b by using a partition 36. In other words, the partition 36 is pipe-shaped and is installed in the middle of the fluid injection space 39 so that the fluid injection space 39 is divided into the internal space 36a and the external space 36b of the partition 36. However, since a height of an upper portion of the partition 36 is smaller than a height of the external chamber 21, the internal space 36a and the external space 36b communicate with each other via the upper portion of the partition 36.

The inlet 37 of the external chamber 31 is connected to the internal space 36a, and the outlet 38 of the external chamber 32 is connected to the external space 36b. Thus, water flowed from the water tank 32 is first stored in the internal space 36a and then is transferred to the external space 36b via the upper portion of the partition 36 and is finally discharged to the outlet 38.

In the apparatus 100 for measuring permittivity of a sample, having the above structure, the sample is prepared using a unique method. Preparation of the sample and installation of a permittivity sensor will now be described with reference to FIGS. 4 and 5.

Figure 4:
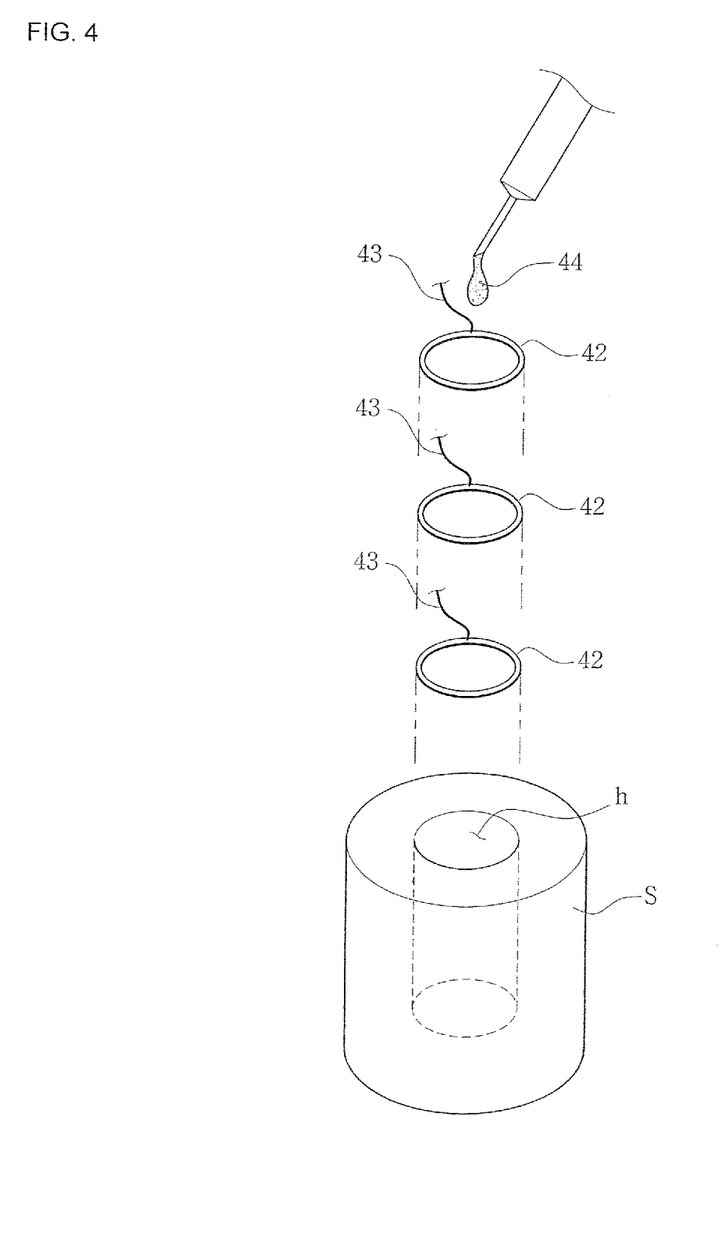
FIG. 4 illustrates an operation of combining a sample with a permittivity sensor.
Figure 5:
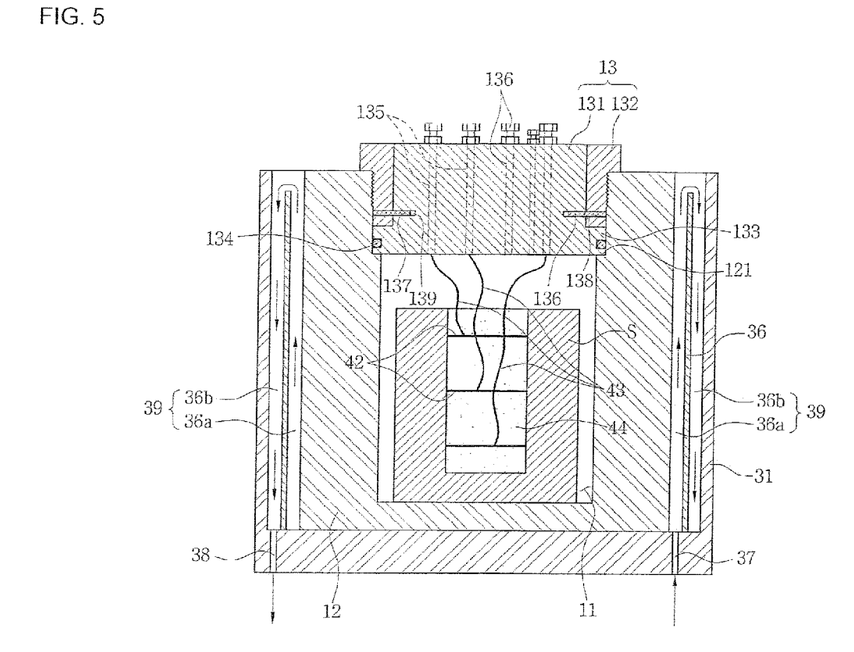
FIG. 5 is a schematic cross-sectional view of the sample chamber in which the sample is put.

FIG. 4 illustrates an operation of combining a sample with a permittivity sensor, and FIG. 5 is a schematic cross-sectional view of the sample chamber in which the sample is put. In the present embodiment, permittivities of various samples may be measured, and in the current embodiment, a rock sample is used as the sample.

Referring to FIGS. 4 and 5, a groove portion h is formed in the middle of a rock sample S that is prepared by coring in a cylindrical shape, along a lengthwise direction of the rock sample S. Of course, a hole (not shown) may be formed in the middle of a rock sample S instead of the groove portion. A plurality of measurement conducting wires 42 having a ring shape are inserted in the groove portion h of the rock sample S. In this regard, the ring-shaped measurement conducting wires 42 are installed to contact an inner circumferential surface of the groove portion h of the rock sample S. Electric wires 43 that are connected to the measurement conducting wires 42 are taken out from the groove portion h and are exposed to the outside. A plurality of measurement conducting wires 42 may be installed, and in the current embodiment, three measurement conducting wires 42 are disposed.

As described above, when installation of the measurement conducting wires 42 is completed, the groove portion h is fully filled with a filling material 44. In the current embodiment, epoxy is used as the filling material 44. When the groove portion h is fully filled with the filling material 44 in this way, the measurement conducting wires 42 are fully sealed, and water should pass through the rock sample S so as to reach the measurement conducting wires 42. In other words, when water pressure increases, water may be permeated into the measurement conducting wires 42 via an air gap of the rock sample S.

The electric wires 43 that are connected to the measurement conducting wires 42 are inserted in different perforation holes 135 that are formed in the body part 131 of the cover 13, respectively. When the plurality of electric wires 43 are inserted in one perforation hole 135 and are disposed adjacent to each other, an error in measurement of permittivity of the rock sample S may occur.

The electric wires 43 are taken out from the sample chamber 10 and are connected to a permittivity sensor 41. A sensor for measuring permittivity of a sample may have various configurations, and in the current embodiment, a time domain reflectometer (TDR) sensor is used as the permittivity sensor 41. The TDR sensor is a well-known sensor and is widely used in measuring the amount of water in soil by measuring permittivity of the sample and thus, detailed description thereof will be omitted.

As water pressure in the sample chamber 10 increased, water is permeated into the rock sample S, and a moisture content of the rock sample S increases, and moisture remains in the measurement conducting wires 42. Thus, the TDR sensor detects a change in permittivity of the rock sample S. The moisture content and porosity of the rock sample S according to pressure and temperature conditions may be measured using the change in permittivity of the rock sample S.

The apparatus 100 for measuring permittivity of a sample illustrated in FIG. 1 includes a data logger 50 and a controller 60. The data logger 50 stores data that is obtained from meters and sensors, is connected to the pressure gauge 26, the thermometer 71, and the permittivity sensor 41 and receives and stores data that is measured therefrom.

The controller 60 performs an arithmetic operation on target data, such as porosity, moisture content or the like of the rock sample S by using the data that is received from the data logger 50 and operates the pump 23 and the temperature adjusting device 33 by varying conditions thereof.

In other words, the state of a stratum or parent rock in which high level radioactive wastes are to be stored may be reproduced by adjusting temperature or water pressure of the space portion 11 when the rock sample S is accommodated in the sample chamber 10. Thus, a moisture content or porosity of the parent rock is calculated so that a waste storage place may be stably designed.

Until now, the apparatus 100 for measuring permittivity of a sample including one sample chamber 10 has been described with reference to FIGS. 1 through 5. However, a plurality of sample chambers may be provided according to embodiments of the present invention.

Figure 6:
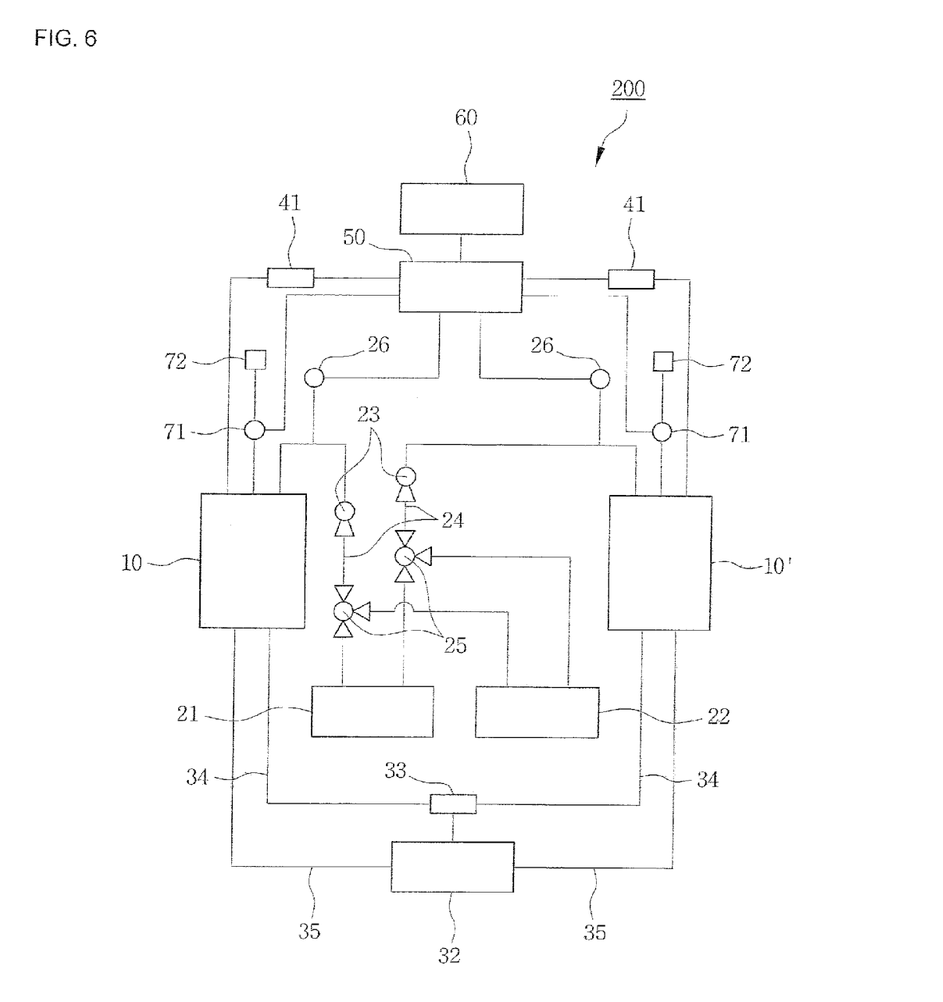
FIG. 6 is a schematic view of an apparatus for measuring permittivity of a sample, according to another embodiment of the present invention.

FIG. 6 illustrates an embodiment in which two sample chambers are disposed. FIG. 6 is a schematic view of an apparatus 200 for measuring permittivity of a sample, according to another embodiment of the present invention.

Referring to FIG. 6, the structure of the apparatus 200 for measuring permittivity of a sample is the same as that of the apparatus 100 for measuring permittivity of a sample illustrated in FIG. 1, and the only difference therebetween is that two sample chambers 10 and 10' are disposed. Although two sample chambers are disposed, all of a pressure adjusting unit including an injection water tank and a discharge water tank, a temperature adjusting unit, a data logger, and a controller are commonly used. However, there is a difference in that a pressure gauge, a thermometer, and a permittivity sensor that are to be attached to the sample chamber are additionally provided. Thus, detailed description of the embodiment illustrated in FIG. 6 will be replaced with description of the previous embodiment illustrated in FIG. 1.

As described above, according to the present invention, physical properties, such as porosity, a moisture content or the like, of parent rocks or stratum in deep underground may be accurately measured by reproducing a similar environment to an environment in underground of stratum or parent rocks in which high level radioactive waste, $CO_2$ or the like are stored, by adjusting temperature and pressure conditions in various ways.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. An apparatus for measuring permittivity of a sample, the apparatus comprising:
    a sample chamber comprising a sealed space portion in which a sample to be measured is put;
    a pressure adjusting unit for varying pressure by applying water pressure to the space portion of the sample chamber;
    a permittivity sensor for measuring permittivity of the sample and disposed outside the sample chamber;
    measurement conducting wires comprising conductors, installed to contact the sample and connected to the permittivity sensor by using electric wires; and
    a data logger for storing data relating to permittivity that is measured by the permittivity sensor.

2. The apparatus of claim 1, wherein the sample chamber comprises a container and a cover for opening or closing the container, and the cover comprises a body part in which a plurality of perforation holes and a connection port for applying the water pressure to the space portion are formed and which is inserted in the container and is combined with the container, and a combination ring that is inserted between an outer circumferential surface of the body part and an inner circumferential surface of the container, is screw-coupled to the container and secures the body part at the container.

3. The apparatus of claim 2, wherein a stepped stopping portion is formed on an inner circumferential surface of the container, and the body part is inserted in the container and is supported on the stopping portion, and a plurality of through holes are formed in the combination ring along a circumferential direction of the combination ring, and a ring-shaped groove portion is formed in an outer circumferential surface of the body part along a circumferential direction of the body part, and a plurality of pins are inserted in the plurality of through holes and are engaged in the groove portion of the body part so that the body part and the combination ring are rotated relative to each other.

4. The apparatus of claim 2, wherein the pressure adjusting unit comprises a pump for pumping high-pressure water into the sample chamber, a connection line for connecting the pump and the connection port to each other, an adjusting valve that is disposed in the connection line and opens or closes the connection line, and a pressure gauge that is installed at the connection line and measures pressure.

5. The apparatus of claim 1, further comprising a temperature adjusting unit for varying temperature of the sample chamber.

6. The apparatus of claim 5, wherein the temperature adjusting unit comprises:
    an external chamber that surrounds the sample chamber, forms a space between the external chamber and the sample chamber and comprises an inlet through which a fluid is injected in the space and an outlet through which the fluid is discharged from the space;
    water tanks in which the fluid is stored and which are connected to the inlet and the outlet of the external chamber, respectively, so that the fluid is circulated; and
    a temperature adjusting unit that is disposed between the water tanks and the external chamber and adjusts temperature of the fluid.

7. The apparatus of claim 5, wherein the temperature adjusting unit comprises:
- an external chamber that surrounds the sample chamber, forms a space between the external chamber and the sample chamber and comprises an inlet through which a fluid is injected in the space and an outlet through which the fluid is discharged from the space; and
- a partition that is ring-shaped and divides a space of the external chamber into an internal space and an external space, wherein the internal space and the external space of the external chamber communicate with each other via an upper portion of the partition, and
- wherein the inlet is connected to the internal space of the partition in a space formed between the external chamber and the sample chamber, and the outlet is connected to the external space of the partition in the space formed between the external chamber and the sample chamber.

8. The apparatus of claim 1, wherein a groove portion is formed in a middle of the sample, and the measurement conducting wires are installed to closely contact the sample along an inner circumferential surface of the groove portion, and after the measurement conducting wires and the electric wires are installed, the measurement conducting wires of the groove portion are sealed by using a filling material that is filled in the groove portion.

9. The apparatus of claim 8, wherein a plurality of measurement conducting wires are ring-shaped, and a plurality of perforation holes are formed in an upper portion of the sample chamber, and the electric wires connected to the measurement conducting wires are taken out from the sample chamber and are exposed to the outside via different perforation holes.

10. The apparatus of claim 8, wherein the filling material comprises epoxy.

11. An apparatus for measuring permittivity of a sample, the apparatus comprising:
- a plurality of sample chambers each comprising a sealed space portion in which a sample to be measured is put;
- a pressure adjusting unit for varying pressure by applying water pressure to the space portion of each of the plurality of sample chambers;
- a permittivity sensor for measuring permittivity of the sample and disposed outside each of the sample chambers;
- measurement conducting wires comprising conductors and installed to contact the sample and connected to the permittivity sensor by using electric wires; and
- a data logger for storing data relating to permittivity that is measured by the permittivity sensor.

* * * * *